(12) United States Patent
Britton et al.

(10) Patent No.: US 8,591,481 B2
(45) Date of Patent: Nov. 26, 2013

(54) MICROFABRICATED INSTRUMENTS AND METHODS TO TREAT RECURRENT CORNEAL EROSION

(75) Inventors: Charles L. Britton, Alcoa, TN (US); Brian R. D'Urso, Clinton, TN (US); Edward Chaum, Memphis, TN (US); John T. Simpson, Clinton, TN (US); Justin S. Baba, Knoxville, TN (US); M. Nance Ericson, Knoxville, TN (US); Robert J. Warmack, Knoxville, TN (US)

(73) Assignees: UT-Battelle, LLC, Oak Ridge, TN (US); University of Tennessee Research Foundation, Knoxville, TN (US)

( * ) Notice: Subject to any disclaimer, the term of this patent is extended or adjusted under 35 U.S.C. 154(b) by 1128 days.

(21) Appl. No.: 12/052,971

(22) Filed: Mar. 21, 2008

(65) Prior Publication Data

US 2009/0240217 A1 Sep. 24, 2009

(51) Int. Cl.
*A61M 5/158* (2006.01)

(52) U.S. Cl.
USPC ........................................................ 604/272

(58) Field of Classification Search
USPC .................................. 604/294, 272; 606/186
See application file for complete search history.

(56) References Cited

U.S. PATENT DOCUMENTS

| | | | |
|---|---|---|---|
| 3,964,482 A * | 6/1976 | Gerstel et al. ............... | 604/890.1 |
| 6,334,856 B1 * | 1/2002 | Allen et al. .................... | 604/191 |
| 6,379,324 B1 * | 4/2002 | Gartstein et al. ................ | 604/22 |
| 6,611,707 B1 * | 8/2003 | Prausnitz et al. ............... | 604/21 |
| 7,150,904 B2 | 12/2006 | D'Urso et al. | |
| 7,273,474 B2 * | 9/2007 | Chang et al. ................... | 604/272 |
| 2002/0138049 A1 * | 9/2002 | Allen et al. .................... | 604/272 |
| 2002/0151774 A1 | 10/2002 | Soller et al. | |
| 2005/0209565 A1 * | 9/2005 | Yuzhakov et al. ............. | 604/173 |
| 2006/0251859 A1 | 11/2006 | D'Urso | |
| 2007/0233016 A1 * | 10/2007 | Kuo et al. ...................... | 604/272 |
| 2007/0260201 A1 * | 11/2007 | Prausnitz et al. .............. | 604/272 |
| 2008/0245764 A1 * | 10/2008 | Pirk et al. .......................... | 216/2 |
| 2008/0249469 A1 * | 10/2008 | Selvaganapathy et al. ... | 604/151 |
| 2008/0269666 A1 * | 10/2008 | Wang et al. ...................... | 604/21 |
| 2008/0312610 A1 * | 12/2008 | Binks et al. .................... | 604/272 |
| 2008/0319404 A1 * | 12/2008 | Pekurovsky et al. .......... | 604/272 |
| 2009/0043279 A1 * | 2/2009 | Kaspar et al. .................. | 604/506 |
| 2009/0054842 A1 * | 2/2009 | Yeshurun et al. .............. | 604/173 |
| 2009/0099502 A1 * | 4/2009 | Tokumoto et al. .............. | 604/21 |
| 2009/0131905 A1 * | 5/2009 | Allen et al. .................... | 604/501 |
| 2009/0143749 A1 * | 6/2009 | Sugimura et al. .............. | 604/272 |
| 2010/0114043 A1 * | 5/2010 | Jung et al. ...................... | 604/272 |

\* cited by examiner

*Primary Examiner* — Susan Su
(74) *Attorney, Agent, or Firm* — Scully, Scott, Murphy & Presser, P.C.

(57) ABSTRACT

In one embodiment, the present invention provides a device and method for treating recurrent corneal erosion. In one embodiment, the method includes the steps of contacting an epithelium layer of a cornea with an array of glass micro-rods including a plurality of sharp features having a length that penetrates a Bowman's layer of the eye, wherein the plurality of sharp features of the array of glass micro-rods produces a plurality of punctures in the Bowman's layer of the eye that are of micro-scale or less. In another embodiment, the present invention provides a method and device for drug delivery. In one embodiment, the device includes an array of glass micro-rods, wherein at least one glass micro-rod of the array of glass micro-rods includes a sharp feature opposite a base of the array of glass micro-rods, wherein the sharp feature includes a treated surface for delivering a chemical compound to the eye.

8 Claims, 4 Drawing Sheets

MICROFABRICATED INSTRUMENTS AND METHODS TO TREAT RECURRENT CORNEAL EROSION

STATEMENT REGARDING FEDERALLY SPONSORED RESEARCH OR DEVELOPMENT

This invention was made with Government support under Contract No. DE-AC05-00OR22725 awarded by the United States Department of Energy. The Government has certain rights in this invention.

FIELD OF THE INVENTION

The present invention in one embodiment relates to surgical instruments. In another embodiment, the present invention relates to a method of treating corneal erosions.

BACKGROUND OF THE INVENTION

Referring to FIG. 1, a corneal abrasion is an injury to the surface epithelium 6 of the cornea 5 that is superficial enough not to involve the basement membrane, i.e., Bowman's layer 10. It is typically due to mechanical trauma, but may also be associated with degenerative changes in the cornea and chronic edema. The defect is seen as superficial on a slit lamp and takes up fluorescence, shining green upon illumination with cobalt blue light. Treatment for uncomplicated abrasions is usually prophylactic antibiotics with pressure patching over 24 hours to decrease the mechanical movement of the blinking lid, which disrupt the epithelial cell growth to heal the defect.

Commonly abrasions heal without complications. However, a significant subset of patients manifest delayed corneal wound healing due to underlying conditions including, but not limited to: tear film deficiency (dry eyes), hypoesthesia (contact lens wearers, history of ocular herpes), scars, and diabetes mellitus.

Many patients exhibit manifestations of recurrent corneal erosions following a primary corneal abrasion. Typically, recurrent corneal erosion occurs in many clinical conditions that affect the corneal surface, such as previous trauma, corneal dystrophies or degenerations, but may also occur spontaneously. Recurrent corneal erosions affect the outermost layer of corneal cells, i.e., the epithelium 6. They occur when the basal layer of epithelial cells adhere poorly to the cornea, causing them to slough off easily. Upon awakening, patients often experience severe pain, blurred vision, and light sensitivity when the eyelid pulls the loosened epithelial cells off the cornea. After the cornea heals, the problem commonly recurs, as the name implies.

The epithelium 5 adjacent to an abrasion or erosion expands via mitosis to fill in the defect. Lesions that are purely epithelial can heal quickly and completely without scarring. Lesions that extend below the Bowman membrane 10 (12 microns thick) are more likely to leave a permanent scar. The epithelial healing process begins when basal epithelial cells undergo mitosis, producing new cells that occupy fresh wounds. Basal cells adhere the epithelium 6 to the stroma 7 in two ways: they secrete the basement membrane, and they contain hemidesmosomes, which are essentially linchpins that protrude through the posterior surface of basal cells and into the stroma 7; each is held in place by an anchoring fibril. Any disruption to basal cell production makes the eye more prone to recurrent erosion.

Recurrent corneal erosion (RCE) syndrome is a condition that is characterized by a disturbance at the level of the corneal epithelial basement membrane i.e., Bowman's layer 10, resulting in defective adhesions and recurrent breakdowns of the epithelium 6. Management of RCE syndrome is usually aimed at regenerating or repairing the epithelial basement membrane to restore the adhesion between the epithelium 6 and the anterior stroma 7. Recurrent corneal erosions occur because there is a defect in the epithelial basement membrane and in hemidesmosome formation, resulting in epithelial loss, microcysts, and bullae formation. They occur after injury, because of improper or inadequate healing of the basement membrane, either because the basal epithelial cells fail to produce proper basement membrane complexes to attach to the Bowman layer 10 and stroma 7 or because of faulty basement membrane adherence. EM studies have shown that during recurrent corneal erosion episodes there is separation of the anchoring system at the level of the epithelial cell membrane or below the level of the anchoring plaques. Normal and degenerate polymorphonuclear leucocytes (PMNs) were found within and between the epithelial cells and within the anchoring layer, i.e. Bowman's layer 10. The degenerate PMNs may secrete metalloproteinases that cleave the Bowman layer 10 below the anchoring system.

Medical management of RCE is aimed at regenerating or repairing the epithelial basement membrane to restore the adhesion between the epithelium 6 and the anterior stroma 7. Typically, treatment is required to promote healing and to relieve the painful symptoms. The healing rate for an abrasion due to RCE syndrome is generally slower than the healing rate for a similar abrasion caused by primary trauma.

Patients with RCE typically respond to topical lubrication therapy, debridement of the epithelium and basement membrane and bandage soft contact lenses. However, many patients may continue to have painful recurrent erosions despite all of these measures. Management includes: placement of a pressure patch over the eyelids for 1 or 2 days and an antibiotic ointment. Sometimes these measures must be followed for several months after resolution of the episode through the use of lubricating and dessicating ointments at bedtime to control symptoms.

In some cases of multiple recurrent erosions, soft contact lenses can be helpful. Bandage lens treatment, if used for this indication, must be continued for up to 8-26 weeks to facilitate repair of the corneal epithelial basement membrane. However, persistent use of soft contact lens increases the risk of infectious corneal disease and is generally deferred until other treatments prove to be ineffective. In some cases, the recurrence of mild corneal erosions may be prevented with the use of hypertonic sodium chloride drops 2%-5% several times during the day and sodium chloride ointment 5% at bedtime.

In resistant cases of RCE, more invasive or surgical intervention is often required. Mechanical debridement, depending on the size of the defect, can be performed, in which a diamond burr is used to "polish" Bowman's membrane 10 after mechanical debridement. The goal of surgical management is superficial debridement to remove the abnormal epithelium 6 and basement membrane, thereby leaving a smooth substrate of the Bowman's layer 10. The adjacent normal epithelium 6 may then be able to resurface in this area, allowing formation of competent attachment complexes and resulting in cessation of erosive symptoms with a reduced frequency of recurrences. In some instances, patients experience reduction of vision and/or recurrent erosions from the ongoing deposition of an abnormal basement membrane and fibrillar collagenous material between the epithelium 6 and Bowman's layer 10.

Laser-based techniques have also been utilized to treat recurrent erosions. These include: excimer laser phototherapeutic keratectomy, excimer laser photoablation, Nd:YAG laser treatment, superficial phototherapeutic keratectomy. These techniques attempt to remove enough of the superficial Bowman layer 10 to permit formation of a new basement membrane with adhesion structures. Surgical superficial keratectomy and penetrating and lamellar keratoplasty have also been performed on rare patients with severe recurrent disease. These technique, although shown to be efficacious, are extremely expensive and not available to the typical ophthalmic practitioner and are rarely used.

SUMMARY OF THE INVENTION

The present invention, in one aspect provides a device and a method for treating recurrent corneal erosions. Recurrent corneal erosions occur because there is a defect in the epithelial basement layer 6 and in hemidesmosome formation, resulting in defective epithelial cell attachment. More specifically, the basal epithelial fail to produce proper basement membrane complexes to attach the Bowman's layer and stroma. Current methods of treating recurrent corneal erosions attempt to enhance epithelial cell attachment, by puncturing the Bowman's layer to induce the formation of a new basement membrane overlying the area's of puncture and/or creating fibrous adhesions to the epithelial cell layer over the scars. Unfortunately, the scaring induced by puncturing the Bowman's layer disrupts the alignment of the collagen fibers in the anterior stroma by inducing new collagen deposition, which reduces the corneal transparency of the areas in which the punctures are produced resulting in white focal scars. It has been determined that the size of the scaring, e.g. white focal scars, is directly related to the size of the puncture device that penetrates through the Bowman layer into the anterior stroma.

In one aspect, the present invention provides a method of treating recurrent corneal erosions that includes contacting an epithelium layer of a cornea with an array of glass micro-rods including a plurality of sharp features, the plurality of sharp features have a length that penetrates a Bowman's layer of the eye, wherein the plurality of sharp features of the array of glass micro-rods produces a plurality of micro-scale punctures in at least the Bowman's layer of the eye. In one embodiment, the present invention provides a method of treating recurrent corneal erosions, in which an array of spikes provide a plurality of punctures through the epithelium and Bowman's layer into the anterior stroma that enhances the ability of basal epithelial cells to maintain the attachment of the cells to the Bowman's layer, wherein the microscopic scars produced by the present invention are visually insignificant in comparison to the scars produced by prior methods for treating recurrent corneal erosions through puncturing the Bowman's layer with a conventional needle. In one embodiment, the method of treating recurrent corneal erosion includes contacting an epithelium layer of a cornea with an array of glass micro-rods each including at least one sharp feature, wherein the at least one sharp feature has a length that extends through the Bowman layer into the anterior stroma of the eye. In one embodiment, the puncturing the epithelial layer and the Bowman layer enhances epithelial cell attachment by inducing the formation of a new Bowman's layer overlying the area of a puncture by the plurality of sharp features and by forming fibrous adhesions to the epithelial layer. The Bowman's layer is the basement membrane layer that is in part deposited by the basal epithelial cells.

In one embodiment, the plurality of sharp features when contacting the epithelium layer extend beyond an interface of the bowman layer and the stroma by a dimension ranging from about 10 microns to about 50 microns.

In one embodiment, the contacting the epithelial layer with the array of glass micro-rods produces a plurality of micro-scale punctures in the epithelial layer and the Bowman's layer. In one embodiment, each micro-scale puncture in the Bowman's layer of the plurality of punctures produced by the array of glass micro-rods has a diameter ranging from about 5 microns to about 100 microns. In another embodiment, each micro-scale puncture in the Bowman's layer of the plurality of punctures produced by the array of glass micro-rods has a diameter ranging from about 10 microns to about 50 microns. In one embodiment, the plurality of punctures have a diameter that results in scaring that would not be visual with the naked eye, i.e., without optical enhancement, such as magnification.

In one embodiment, the number of glass micro-rods and the spacing between adjacent glass micro-rods is selected to provide a ratio of punctures on the order of approximately one puncture to one basal cell, wherein the basal cells have a diameter of approximately 15 microns. In one embodiment, the number of glass micro-rods ranges from about 400 glass micro-rods to about 100,000 glass micro-rods. In one embodiment in which the plurality of glass micro-rods ranges from about 400 glass micro-rods to about 100,000 glass micro-rods, the pitch ranges from about 5 microns to about 15 microns, wherein the pitch is equal to the dimension separating adjacent glass micro-rods.

In another aspect, the present invention provides a medical device for treating recurrent corneal erosions. In one embodiment, the medical device for treating recurrent corneal erosions includes an array of glass micro-rods including a sharp feature opposite a base of the array of glass micro-rods, the sharp feature having a length that penetrates a Bowman's layer of an eye and having a diameter that produces a puncture in the Bowman's layer of micro-scale or less.

In one embodiment, the glass micro-rods are made of a silica containing material. In one embodiment, the glass micro-rods are composed of soda-lime silicate glass, borosilicate glass, leaded glass or a combination thereof.

In one embodiment, the length of the plurality of sharp features is less than 50 microns. In one embodiment, the array of glass micro-rods includes a plurality of glass micro-rods that includes about 400 to about 100,000 glass micro-rods, wherein each glass micro-rod includes a sharp feature. Therefore, a single contact of the array of glass micro-rods to the corneal produces on the order of approximately 400 to approximately 100,000 punctures in the Bowman's layer of the eye. In one embodiment, the array of glass micro-rods includes a plurality of glass micro-rods, wherein adjacent glass micro-rods are separated by a distance ranging from about 10 microns to about 40 microns.

In one embodiment, the array of glass micro-rods extends from the base. In one embodiment in which the array of glass micro-rods includes about 400 to about 100,000 micro-rods and the adjacent glass micro-rods are separated from one another by a distance ranging from about 10 microns to about 40 microns, the base may have a width ranging from about 1 mm to about 3 mm, and a length ranging from about 1 mm to about 3 mm. In one embodiment, when the base has a circular geometry, the base has a diameter ranging from about 1 mm to about 3 mm.

In one embodiment, the sharp feature of the glass micro-rod is angled from the plane that is normal to the base of the array of glass micro rods or is normal to the base of the array of glass micro rods.

In another aspect, the present invention provides a method for delivering drugs or applying gene therapy to an eye. In one embodiment, the method includes contacting a cornea of an eye with an array of glass micro-rods including a plurality of sharp features, wherein the sharp features are treated to incorporate on their surfaces a chemical compound for delivery to the eye. In one embodiment, the surface of the glass micro-rods being a negatively charged surface engages chemical compounds having a positive charge through mechanisms of electrostatic attraction. In other embodiments, the surface of the glass micro-rods may be functionalized to provide a positive charged surface that attracts negatively charged chemical compounds.

In one embodiment, the treated surface includes an epithelial growth factor, wherein when the array glass micro-rods is contacted to a defect in an epithelium layer, the epithelial growth factor enhances wound healing and epithelial resurfacing in the defect in the epithelium layer.

In another embodiment, the treated surface includes an antiangiogenic factors, wherein when the array of glass micro-rods is contacted to the cornea, the antiangiogenic inhibits corneal neovascularization.

In a further embodiment, the treated surface includes at least one of a steroid or steroid depots for post-operative corneal graft management.

In yet another embodiment, the treated surface includes at least one of an antibiotics or antiviral agent, wherein when the array of glass micro-rods is contacted to the cornea, the antibiotics or the antiviral agent promote healing of infectious lesions.

In an even further embodiment, the treated surface includes mitotic inhibitors, wherein when the array of glass micro-rods is contacted to the cornea, the mitotic inhibitors treat pterygia.

In yet an even further embodiment, the treated surface includes collagenase inhibitors, wherein when the array of glass micro-rods is contacted to the cornea the collagenase inhibitors treats corneal melts.

In yet another embodiment, the treated surface includes at least one of a viral and non-viral vectors for gene therapy to the cornea and the eye.

In another aspect, the present invention provides a medical device for delivering drugs to an eye. In one embodiment, the medical device may be employed in the above described drug delivery method. In one embodiment, the medical device includes an array of glass micro-rods having a sharp feature opposite a base of the array of glass micro-rods, wherein the sharp feature includes a surface that has been treated to deliver a chemical composition to the eye. In one embodiment, the sharp feature has a length to deliver drugs or gene therapy to at least one of the epithelium layer and stroma layer of an eye. In one embodiment, the treated surface includes at least one of epithelial growth factors, antiangiogenic factors, steroids and steroid depots, antibiotics and antiviral agent depots, mitotic inhibitors, collagenase inhibitors, or viral and non-viral vectors.

BRIEF DESCRIPTION OF THE DRAWINGS

The following detailed description, given by way of example and not intended to limit the invention solely thereto, will best be appreciated in conjunction with the accompanying drawings, wherein like reference numerals denote like elements and parts, in which.

DETAILED DESCRIPTION OF THE INVENTION

Figure 1:
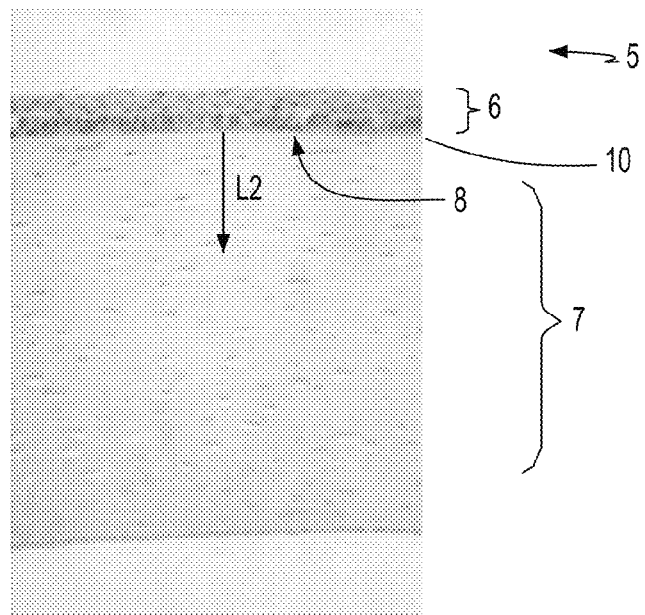
FIG. 1 is a side cross section view of a cornea.

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

In one embodiment, the present invention relates to structures and methods for treating recurrent corneal erosions. In another embodiment, the present invention relates to structures and devices for drug and gene therapy delivery. When describing the following structures and methods, the following terms have the following meanings, unless otherwise indicated.

The term "glass" denotes a non-crystalline solid.

The term "micro-rod" denotes a structure having a height of less than 100 microns and having an aspect ratio of length to width on the order of approximately 2:1 or greater, wherein a cross section perpendicular to the height is multi-sided or arcular geometry.

The term "micro-scale" denotes a dimension of less than about 1 mm.

The term "macro-scale" denotes punctures in the Bowman layer having a diameter greater than or equal to 1 mm.

The term "Bowman's layer" denotes the basement membrane layer of the corneal epithelium.

The phrase "sharp feature" is defined herein to mean a tapered structure that terminates into a point. In one embodiment, the sharp surface feature tapers from a base portion having a first cross sectional area to a point portion opposite the base portion having a reduced cross sectional area that is no more than 30% of the first cross sectional area, such as 25%, 20%, 15%, 10%, 8%, 6%, 5%, 4%, 3%, 2%, 1%, or less than 1% of the first cross sectional area. In one embodiment, the sharp surface feature is a spike. In one embodiment, a spike has a base with a circumferential geometry and a tip with a circumferential geometry.

The term "cannula" means a shaft supporting the array of glass micro-rods.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper", "lower", "right", "left", "vertical", "horizontal", "top", "bottom", and derivatives thereof shall relate to the invention, as it is oriented in the drawing figures.

Recurrent corneal erosions occur because there is a defect in the epithelial basement membrane and in hemidesmosome formation, resulting in defective epithelial cell attachment open. In one embodiment, the basal epithelial cells fail to produce proper basement membrane complexes to attach to the Bowman's layer. In one embodiment, the present invention enhances epithelial cell attachment by inducing the formation of new basement membrane overlying the areas of the puncture and by creating fibrous adhesions to the epithelial cell layer.

Prior to the present invention, typically in the most severe cases of recurrent corneal erosion, the use of anterior stromal puncture (ASP) has been advocated. Anterior stromal puncture (ASP) is a technique that uses a small gauge needle (HOW BIG) is used to induce the formation of many small scars at the level of Bowman's membrane. This procedure involves making 75-150 punctures with a 25 to 30 gauge needle through the epithelium and the Bowman membrane into anterior stroma. The needle tip is inserted through the epithelial defect, making small punctures into the anterior stroma. More specifically, a Rubenfeld needle tip is inserted through the epithelial defect, making approximately macro-scale punctures through Bowman's layer (12 microns thick) into the anterior stroma.

Figure 2:
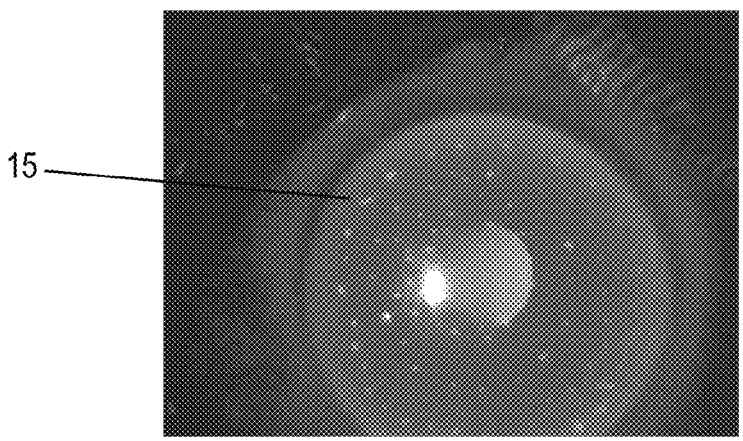
FIG. 2 is a front pictorial view of corneal scarring that results from prior stromal puncture techniques.
Figure 3:
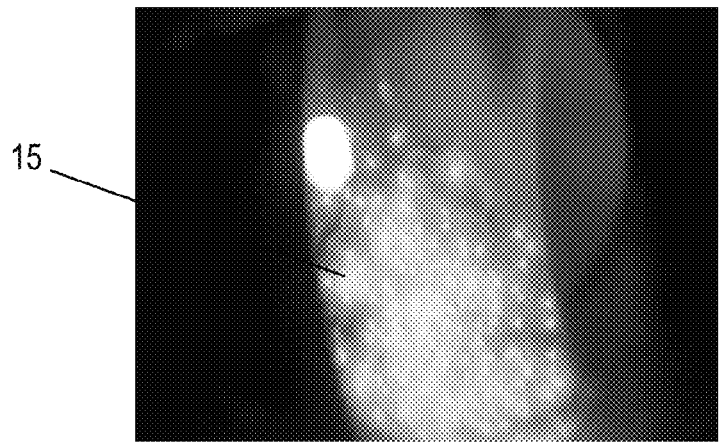
FIG. 3 is front pictorial view of corneal scarring that results from repeated stromal puncture treatments.

Typically, the scarring induced by puncturing the Bowman's layer with the above-described needles in anterior stromal puncture (ASP) disrupts the alignment of the collagen fibers in the anterior stroma by inducing new collagen deposition, which reduces the corneal transparency of the areas in which the punctures are produced resulting in white focal scars 15. FIGS. 2 and 3, depicts the visible scars formed using anterior stromal puncture formed by ASP are on the macro-scale.

Further, referring to FIGS. 2 and 3, contiguous treatment induce a large geographic region of scarring with significant refractive and optical consequences for vision. The scarring induced by anterior stromal puncture (ASP) occurs due to loss of corneal transparency in these areas. The puncture disrupts the orderly alignment of collagen fibers in the anterior stroma by inducing new collagen deposition, creating a white focal scar. The size of the scar is directly related to the size of the defect produced in the anterior stroma by the needle tip.

In one embodiment, the present invention punctures the Bowman's layer without producing the scarring that results from anterior stromal puncture (ASP). In one embodiment, the present invention provides a medical device that induces focal defects in the Bowman's layer (having a thickness of about 10 microns or less) with minimal penetration of the anterior stroma (about 10 microns to 50 microns into the anterior stroma); induces diffuse micro-scale scars having dimensions below the visual threshold; and enhances the attachment of each basal epithelial cell.

Figure 4:
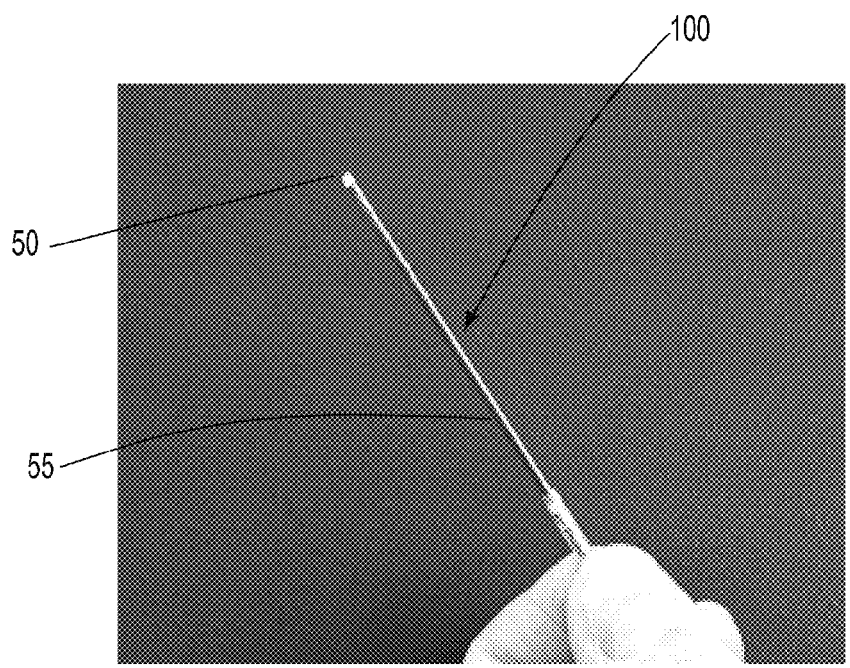
FIG. 4 is a perspective view of one embodiment of a medical device for treating recurrent corneal erosions, in accordance with one embodiment of the present invention.

FIG. 4 depicts one embodiment of a medical device 100 for treating recurrent corneal erosions. In one embodiment, the medical device 100 includes an array of glass micro-rods 50 that are positioned at an end of a cannula 55 for contacting the epithelium. More specifically, in one embodiment, the array of glass micro-rods 50 is positioned so that the array of glass micro-rods 50 may be manipulated to contact and puncture, i.e., penetrate the epithelium 6 and the Bowman layer 10. In one embodiment, the puncturing of the epithelial layer 6 and the Bowman layer 10 into the anterior stroma 7 enhances epithelial cell attachment by inducing the formation of a new Bowman's layer overlying area of a puncture by the plurality of sharp features and by forming fibrous adhesions to the epithelial layer 6. In one embodiment, the punctures induce the secretion of new BM proteins by the epithelial cells.

Figure 5:
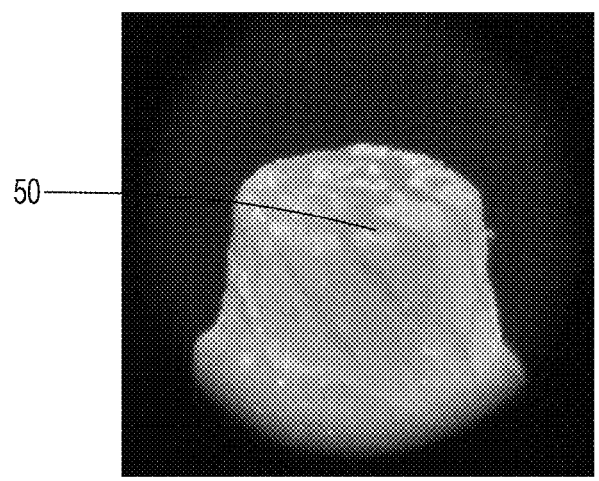
FIG. 5 is a perspective view of one embodiment of a medical device including a glass micro-rod array for treating recurrent corneal erosions, in accordance with one embodiment of the present invention.

FIG. 5 is a magnified perspective view of one embodiment of an array of glass micro-rods 50. In one embodiment, the array of glass micro-rods 50 may be provided by a base having a diameter equal to about 3 mm, wherein the base has on the order of approximately 100,000 or less micro-rods. In one embodiment, the glass micro-rods have an aspect ratio of length to width on the order of about 5:1 or greater. In another embodiment, the glass micro-rods have an aspect ratio of length to width on the order of about 10:1 or greater. In another embodiment, the glass rods have an aspect ratio of length to width on the order of about 100:1.

Figure 6:
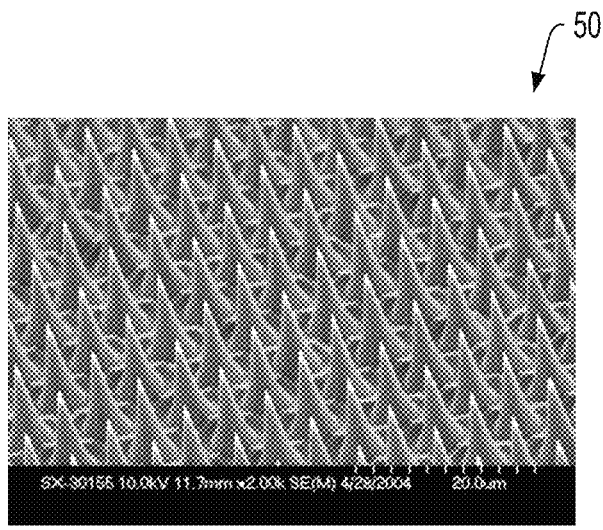
FIG. 6 is a micrograph of one embodiment of a sharp feature, in which the length of the glass micro-rods is normal to the base of the array of glass micro-rods, in accordance with the present invention.

FIG. 6 is a magnified view of one embodiment of glass micro-rod 50 including a sharp feature 51. In one embodiment, the length of the plurality of sharp features is less than 50 microns. In another embodiment, length of the plurality of sharp features ranges from about 20 microns to about 50 microns. In an even further embodiment, the length of the plurality of sharp features ranges from about 10 microns to about 20 microns.

In one embodiment, the separation between adjacent glass micro-rods is selected to provide that each glass micro-rods contacts a basal cell during penetration. In one example, when the basal cell diameter is equal to approximately 15 microns, the separation between adjacent glass micro-rods is equal to approximately 15 microns so that each basal cell is contacted by the each glass micro-rod during the application of the array of glass micro-rods to the corneal. In one embodiment, the array of glass micro-rods includes a plurality of glass micro-rods, wherein adjacent glass micro-rods are separated by a distance ranging from about 10 microns to about 40 microns. In another embodiment, the array of glass micro-rods 50 includes a plurality of glass micro-rods, wherein adjacent glass micro-rods are separated by a distance ranging from about 10 microns to about 20 microns. In an even further embodiment, the array of glass micro-rods 50 includes a plurality of glass micro-rods, wherein adjacent glass micro-rods are separated by a distance ranging from about 10 microns to about 15 microns. In another embodiment, the adjacent glass micro-rods are separated by a distance ranging on the order of about 15 microns.

In one embodiment, the sharp feature 51 tapers from a base portion 52 having a first cross sectional area to a point portion 53 opposite the base portion 52 having a reduced cross sectional area that is no more than 30% of the first cross sectional area.

In one embodiment, the sharp feature 51 extends the entire length of the glass micro-rod to provide the geometry of the spike. In one embodiment, a spike has a base with a circumferential geometry and a tip with a circumferential geometry. In another embodiment, the base portion 52 may have a multisided geometry, such as a hexagonal shape.

Figure 7:
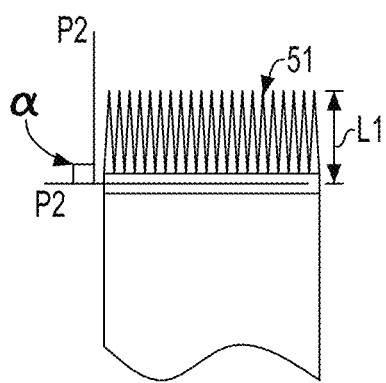
FIG. 7 is a side cross sectional view of one embodiment of a medical device in which the length of the glass micro-rods is normal to the base of the array of glass micro-rods, in accordance with the present invention.

FIG. 7 is a side cross-section view of an array of glass micro-rods 50, in which the sharp feature 51 of each glass micro-rod is normal to a base 10 of the array of the glass micro-rods 50. The term "normal" as used herein means that the plane P1 parallel to the length L1 of the sharp feature 51 and the plane P2 that is parallel to the width of the base 10 of the array of glass micro-rods 50 intersect at an angle α that is equal to approximately 90 degrees. It is noted that although, the sharp feature 51 is depicted in the supplied figures as extending the entire length of each of the glass micro-rods, embodiments of the present invention have been contemplated that include where the sharp feature only extends along a portion of the length of the glass micro-rods. In one embodiment, the sharp features of the glass micro-rods 50 that are normal to the base 10 of the array of glass micro-rods 50 may be referred to as a vertically aligned array of glass micro-rods.

Figure 8:
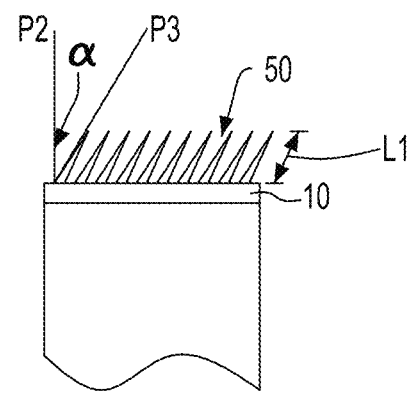
FIG. 8 is a side cross sectional view of one embodiment of a medical device in which the glass micro-rods are angled, in accordance with the present invention.

FIG. 8 is a side cross-section view of an array of glass micro-rods, in which the sharp feature 51 of each glass micro-rod is angled. In one embodiment, the angle at which each sharp feature 51 is positioned may be defined by the angle α at the intersection of a plane parallel $P_1$ to the length $L_1$ of the sharp feature 51 of the glass micro-rod and a plane $P_2$ that is normal to the base 10 of the array of micro-rods 50. In one embodiment, the base 10 of the array of glass micro-rods 50 is connected to the cannula 55. In one embodiment, the length $L_1$ of the sharp feature 51 extends from the base portion 52 of the glass micro-rod to the point portion 53 of the glass micro-rod. It is noted that although, the sharp feature 51 is depicted in the supplied figures as extending the entire length of each of the glass micro-rods, embodiments of the present invention have been contemplated that include where the sharp feature only extends along a portion of the length of the glass micro-rods.

Still referring to FIG. 8, in one embodiment, the plane $P_3$ that is parallel to the length $L_1$ of the sharp feature 51 may be angled a from about 0° to about 70° from a plane $P_2$ that is normal to a face of the base 10 of the array of glass micro-rods 50. In another embodiment, the plane $P_3$ that is parallel to the length $L_1$ of the sharp feature 51 may be angled from about 15° to about 55° from a plane $P_2$ that is normal to a face of the base 10 of the array of glass micro-rods 50. In a farther embodiment, the plane $P_3$ that is parallel to the length $L_1$ of the sharp feature 51 may be angled from about 30° to about 60° from a plane $P_2$ that is normal to a face of the base 10 of the array of glass micro-rods 50.

Figure 9:
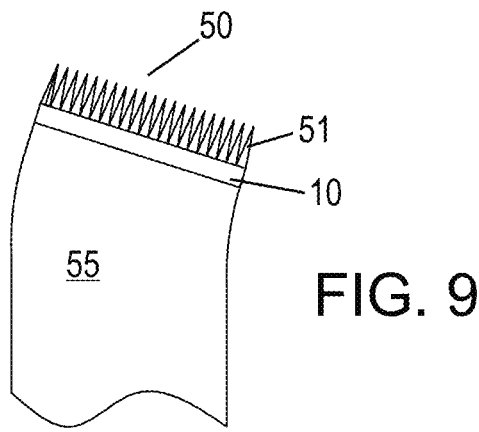
FIG. 9 is a side cross sectional view of one embodiment of a medical device in which the length of the glass micro-rods is normal to the base of the array of glass micro-rods and there is a curvature in the cannula, in accordance with the present invention.

FIG. 9 depicts another embodiment of a medical device 100 for treating recurrent corneal erosions including an array of glass micro-rods 50 having a sharp feature 51 that is configured to be normal to a base 10 of the array of glass micro-rods 50, wherein the cannula 55 includes a curvature to angle the array of glass micro-rods.

In another aspect of the present invention, a method of manufacturing a medical device is provided. In one embodiment, the sharp features of the array of glass micro-rods is provided by a composite material that is etched using a selective etch process. The composite material may be made from any two components that provide suitable differential etching characteristics relative to one another. Suitable materials include, for example, glasses, metals (including alloys), ceramics, polymers, resins, and the like. In one embodiment, the composite material may include a recessive component and a protrusion component, wherein the recessive component is etched selective to the protrusion component. In one embodiment, the composite material includes a core, such as rods, and a matrix, such as cladding present on the exterior of the rod.

In one embodiment, the protrusive component is a core of the composite material. In one embodiment, the protrusive component of the composite material may be composed of glass rods composed of Corning 0120. Corning 0120 is composed of a $K_2$—O—PbO—$B_2$—$O_3$—$SiO_2$ system. It is noted that other materials may be suitable for the protrusive component, so long as the material selected etched at a slower rate than the recessive component. In one embodiment, the recessive component is present on the exterior of the core of the protrusive component. In one embodiment, the recessive component of the composite material may be composed of a cladding composed of Corning 8161. Corning 8161 is composed of about 51 wt. %, PbO, about 39 wt. % $SiO_2$, about 6 wt. % $K_2O$, and about 2 wt. % KaO. The two glassed are differentially etched such that the cladding glass is etched away from the core glass, while the core glass gets sharpened (tapered) by the etching process. It is noted that the above glass compositions are noted for illustrative purposes only and are not intended to limit the scope of the present invention, since other compositions have been contemplated and are within the scope of the present invention. One factor that is considered in selecting glass compositions for use with the present methods and structures includes that the glass compositions selected for the core, i.e., protrusive component, and the cladding, i.e., recessive component, should be "drawable", i.e. their softening temperature ranges should overlap. In one embodiment, a carbon nanotube structure may be used, as opposed to a glass composition to provide the micro-rods.

In one embodiment, the recessive component of the composite material is etched selective to the protrusion component. Etch selectively means that one component, i.e., the recessive component of the composite material, is etched at a faster rate than a second component, i.e., the protrusion component. In one embodiment, the etchant is composed of an:organic or inorganic acid or alkali; polar, nonpolar, organic, inorganic, or mixed solvent; or mixtures of any of the foregoing. The etchant is preselected to selectively etch the composite material as described herein. For example, an acid such as HF, HCl, HBr, or HI is selected to differentially etch glass compositions.

In one embodiment, the etchant is composed of a "mixed etchant system" which includes of a mixture of a plurality of etchants that provide selective etch contrast ratios when applied to the composite material. For example, in one embodiment the etchant can selectively etch one phase while the other etchant can selectively etch the other phase. One example of a mixed etchant system is a mixture of HF and HCl.

In another embodiment, a plurality of etchants can be used in a series of two or more sequential etching steps. For example, in one embodiment HF is applied to the composite material in a first etching step, rinsed away, and then HCl is applied to the composite material in a second etching step.

In one embodiment when the composite material is composed of a core, e.g., rods of a protrusive component, and a matrix, e.g., cladding material of a recessive material, prior to etching the core and the matrix are bundled into an aligned array (hereafter referred to as a bundle). In one embodiment, the matrix has a multi-sided, e.g., hexagonal, cross-sectional shape to minimize voids while the core has a circular cross-section. In another embodiment, the matrix has a circular cross-section. In one embodiment, the matrix material and core material are selected based on differential etchability, wherein the core material has a lower etch rate than the matrix material, and forms protrusive, sharp features upon etching of the composite material.

In one embodiment, the bundle can heated to a temperature sufficient to soften the materials comprising the bundle, but low enough to avoid damage, decomposition, or other deleterious changes. In one embodiment, the temperature of the glass should be heated to the glass transition temperature ($T_g$). In one embodiment, the bundle is then drawn along the axis of the bundled rods to fuse and reduce the diameter of the bundle. In one embodiment, the drawn bundle has reduced size matrix material and core material.

The drawn bundle is cut transversely into sections that can be re-bundled to increase the number of core material cores in the cross-section thereof. In a following process step, the bundle can then be drawn again. In one embodiment, it is noted that a twice-drawn bundle has further reduced size matrix material and core material. The twice-drawn bundle may then be cut transversely into sections that are re-bundled to further increase the number of cores in the cross-section thereof. It is noted that the process of bundling, drawing, and cutting can be performed a single time or repeated many times until the desired diameter and spacing of the core material is obtained.

In one embodiment, after the final draw (which may be the first draw), the bundle can be cut, bundled, and fused in order to obtain a larger diameter bundle. Thereafter, the bundle can be transversely cut to produce slices (plates, tiles) of any desired thickness.

Subsequently, in one embodiment, one or both of the cut (composite) surfaces of the bundle are etched to create an array of sharp features composed of core material on one or both sides of the cut bundle. The composite surface can be contacted with an etchant, (HF, for example), which etches the matrix material (recessive component) faster than the core material (protrusive component). The etching continues until the matrix material is etched back to the desired depth, leaving some of the core material protruding from the surface. The result is that the core material is sharpened to a cone-shaped spike that provides the sharp feature 51 that extends from a base 10. In one embodiment, the aspect ratio of the spike is dependent on the ratio of the matrix material and core material etch rates. Hereafter, the composite material that has been etched to provide the sharp features that extend from the base is referred to as the array of glass micro-rods.

In a following step the base 10 of the array of glass micro-rods 50 is connected to the cannula 55. In one embodiment, the cannula 55 provides the structure through which the array of glass micro-rods 50 may be manipulated in contacting the eye. In one embodiment, the cannula 55 provides a handle. In one embodiment, the attachment of the array glass micro-rods 50 is connected to the cannula 55 by adhesive. In one embodiment in which the sharp feature 51 of the array of glass micro-rods 50 are positioned normal to the base 10 of the array of glass micro-rods 50, the base 10 of the cannula 55 may be angled relative to cannula to provide an angle β at the intersection of the plane parallel to the length of the sharp features and the plane parallel to the length of the cannula. In one embodiment, the cannula has a diameter that is suitable for insertion into on eye. In one embodiment, the cannula has a diameter of 5 mm or less. In another embodiment, the cannula has a diameter of 3 mm or less.

In another aspect, the present invention provides a method of treating recurrent corneal erosions. In one embodiment, the method of treating recurrent corneal erosions includes contacting an epithelium layer 6 of a cornea 5 with an array of glass micro-rods 50 including a plurality of sharp features 51, wherein the sharp features 51 have a length L2 that engages at least the Bowman layer 10 of the eye.

In one embodiment, the contacting of the epithelial layer 6 includes puncturing the epithelial layer 6 and the Bowman layer 10 into the stroma 7 to enhance epithelial cell attachment by inducing the formation of a new Bowman's layer overlying area of a puncture by the plurality of sharp features 51 and by forming fibrous adhesions to the epithelial layer. In one embodiment, puncturing the basal cells of the epithelial layer results in the secretion of BM proteins, which produces the new Bowman layer.

Referring to FIG. 1, in one embodiment, when the array of glass micro-rods 50 contact the epithelium layer 6, the points of the sharp features 51 of the plurality of glass micro-rods 50 extend beyond an interface 8 of the bowman layer 10 and the stroma 10 by a dimension L2 of less than about 50 microns. In another embodiment, when the array of glass micro-rods contact the epithelium layer, the points of the sharp features 51 of the plurality of glass micro-rods 50 extend beyond an interface 8 of the bowman layer 10 and the stroma 10 by a dimension L2 ranging from about 10 microns to about 50 microns. In an even further embodiment, when the array of glass micro-rods 50 contact the epithelium layer 6, the points of the sharp features 51 of the plurality of glass micro-rods 50 extend beyond an interface 8 of the bowman layer 10 and the stroma 10 by a dimension L2 ranging from about 10 microns to about 30 microns. In one embodiment, the punctures through the epithelial layer 6 and the Bowman's layer 10 into the anterior stroma 7 enhance epithelial cell attachment, wherein the puncturing induces the formation of a new basement membrane corresponding to the area's of puncture and/or creating fibrous adhesions to the epithelial cell layer 6.

In one embodiment, the contacting the epithelial layer 6 with the array of glass micro-rods 50 produces a plurality of punctures in the epithelial layer 6 and the Bowman's layer 10, wherein each puncture of the plurality of punctures a submicron dimension. It is noted that the actual diameter of the puncture depends on both the sharp features diameter as passing through the epithelial layer 6 and the Bowman's layer 10.

For example, in one embodiment, in which the sharp feature 51 extends the entire length L1 of the glass micro-rod 50, the tip of the sharp feature 51 of the glass micro-rod 50 has a diameter that is less than 100 nm, but the diameter increases in the direction towards the base of the glass micro-rods 50 to a diameter that may be on the order of approximately 1 micron. In this example, the diameter of the punctures in the epithelial layer 6 produced by this sharp feature 51 depends upon the depth at which the sharp feature penetrates beyond the interface of the bowman layer 10 and the stroma 10, which can range from less than 100 nm to 1 micron.

In one embodiment, the contacting the epithelial layer 6 with the array of glass micro-rods 50 produces a plurality of punctures in the epithelial layer 6 and the Bowman's layer 10, wherein each puncture of the plurality of punctures has a diameter ranging of less than fifty microns. In one embodiment, the contacting the epithelial layer 6 with the array of glass micro-rods 50 produces a plurality of punctures in the epithelial layer 6 and the Bowman's layer 10, wherein each puncture of the plurality of punctures has a diameter ranging from less than 1 micron to fifty microns. In another embodiment, the contacting the epithelial layer 6 with the array of glass micro-rods 50 produces a plurality of punctures in the epithelial layer 6 and the Bowman's layer 10, wherein each puncture of the plurality of punctures has a diameter ranging from about 1 microns to about 10 microns. In one embodiment, the plurality of punctures have a diameter that results in scaring are not be visual with the naked eye, i.e., without optical enhancement, such as magnification.

In one embodiment, the contacting the epithelial layer 6 with the array of glass micro-rods 50 produces a plurality of punctures in the epithelial layer 6 and the Bowman's layer 10, wherein the plurality of punctures ranges from about 400 to about 100,000. In another embodiment, the contacting the epithelial layer with the array of glass micro-rods 50 produces a plurality of punctures in the epithelial layer 6 and the Bowman's layer 10, wherein the plurality of punctures ranges from about 400 to about 4,000.

In one embodiment, the method and devices for treating recurrent corneal erosion as described above induce focal defects in the Bowman's layer 10 with minimal penetration of the anterior stroma 7; induce diffuse micro-scale scars without disadvantageous visual, refractive or anatomical complications; have sharp features that engage the eye to a specified depth, i.e., about 10 microns to about 50 microns, preferably being less than 30 microns, as measured from the interface 8 of the Bowman's layer 10 and the anterior stroma 7; and enhance attachment of every basal epithelial cell.

In another aspect, the present invention provides methods and structures for delivering or applying drug and gene therapy. In one embodiment, a medical device for delivering or applying drug and/or gene therapy includes an array of glass micro-rods, wherein at least one glass micro-rod of the array of glass micro-rods includes a sharp feature opposite a base of the array of glass micro-rods, wherein the sharp feature includes a treated surface (which in some embodiments may be referred to as a drug delivery surface) for delivering a chemical composition to the eye. In one embodiment, the above-described array of glass micro-rods includes the delivery of therapeutic drugs or gene therapy to the basal epithelium 6 and anterior stroma 7. Directed delivery of drugs to the corneal stroma 7 as local depots, and basal epithelial tissues may improve the treatment and management of numerous diseases. In one embodiment, the exterior surface of the sharp features of the array of glass micro-rods are easily doped with drugs and gene delivery vectors. In one embodiment, functionalization, i.e., engagement of the drug or gene treatment compositions, is dependent upon the charge of the surface of the glass micro-rod. In one embodiment, in which the glass surface has a negatively charged surface, compounds of the drug or gene treatment compositions having a positively charged surface are engaged to the glass surface by electrostatic attraction. In one embodiment, in which the glass surface has a positive charged surface, compounds of the drug or gene treatment compositions having a negatively charged surface are engaged to the glass surface by electrostatic attraction. In another embodiment, the charge of the glass surface of the glass micro-rods may be doped or coated to provide the desired charge.

In one embodiment, the surface of the sharp features is functionalized, in which DNA is dried on the surface of the sharp feature or sharp features 51 of the array of glass micro-rods 50. In one embodiment, the water plasma produces a hydropholic surface on the sharp feature 51, wherein DNA in water solution spreads and dries onto the surface of the sharp features 51 of the array of glass micro-rods 50. In one embodiment, as the functionalized surface of the sharp features 51 penetrate into the cells of the eye some of the DNA is released and is expressible.

In another embodiment, the surface of the sharp features 51 may be functionalized using binding strategies. For example, in one embodiment, organic molecules may be grafted onto inorganic surfaces, such as the sharp features of the array of glass micro-rods. In one embodiment, functionalization may include the reaction of trialkoxysilyl with silanol groups that are present on the surface of the sharp features of the array of glass micro-rods. In one embodiment, silanols are generally synthesized on the surface of the glass micro-rods 50 by hydrolysis of halosilane, alkoxysilane, or aminosilane; by oxidation of hydrosilane; or by hydrolysis of arylsilane in the presence of strong acid. In another embodiment, surface functionalization includes the preparation of a chlorinated inorganic surface followed by a reaction with organometallic compounds, such as grignard reagents.

In another embodiment, the surface of the glass micro-rods 50 is functionalized using protein soaks. In one embodiment, the protein soak may include poly-L-lysine or fibronectin, wherein the former has a positive charge that is attracted to negatively charged surface of the array of glass micro-rods 50. In another embodiment, the surface of the glass micro-rods is functionalized using organosilanes, such as, for example APTES.

In one embodiment, the treated surface includes an epithelial growth factor, wherein when the array glass micro-rods 50 is contacted to a defect in an epithelium layer, the epithelial growth factor enhances wound healing and epithelial resurfacing in the defect in the epithelium layer. In one embodiment, the defect to which the epithelial growth factor is applied includes at least one of abrasions, erosions, and/or neurotrophic keratitis. Examples of epithelial grown factor include epidermal growth factor, multiple fibroblast growth factors, and insulin like growth factor.

In another embodiment, the treated surface includes antiangiogenic factors, wherein when the array of glass micro-rods is contacted to the cornea, the antiangiogenic inhibit corneal neovascularization. Examples of antiangiogenic include at least one of Avastin, Leucentis, Macugen, and/or other anti-VEGF molecules.

In a further embodiment, the treated surface includes at least one of a steroid or steroid depots for post-operative corneal graft management.

In yet another embodiment, the treated surface includes at least one of an antibiotics or antiviral agent, wherein when the array of glass micro-rods is contacted to the cornea, the antibiotics or the antiviral agent promote healing of infectious lesions. Examples of antibiotic or antiviral include but are not limited to: herpetic, fungal, and bacterial keratitis).

In yet a further embodiment, the treated surface includes mitotic inhibitors, wherein when the array of glass micro-rods is contacted to the cornea, the mitotic inhibitors treat pterygia. Examples of mitotic inhibitors to treat pterygia including, but are not limited to 5-FU, methotrexate, or other molecules that inhibit cell proliferation.

In yet a further embodiment, the treated surface includes collagenase inhibitors, wherein when the array of glass micro-rods is contacted to the cornea the collagenase inhibitors treat corneal melts.

In yet a further embodiment, the treated surface includes at least one of viral and non-viral vectors for gene therapy to the cornea. For example, viral and non-viral vectors for gene therapy to the cornea include, but are not limited to AAV, lentivirus and dendrimers and other non-viral DNA-condensing vehicles.

The present invention provides medical devices and related methods for recurrent corneal erosions that only induce visually insignificant, microscopic scars. The present devices are generally characterized by an array of glass micro-rods or spikes having tissue engaging components, e.g., sharp features, of a specified depth. In one embodiment, by contacting cornea with such device, the present invention provides improved treatment of recurrent corneal erosions because the treatment (1) induces focal defects in Bowman's layer with minimal penetration of the anterior stroma, (2) induces diffuse microscopic scars without visual, refractive or anatomical complications, and (3) enhances the ability of individual basal epithelial cells across the surface of the cornea to maintain the attachment to Bowman's layer.

The following examples are provided to further illustrate aspects of the present invention and demonstrate some advantages that arise therefrom. It is not intended that the invention be limited to the specific examples disclosed.

EXAMPLES

Figure 10A:
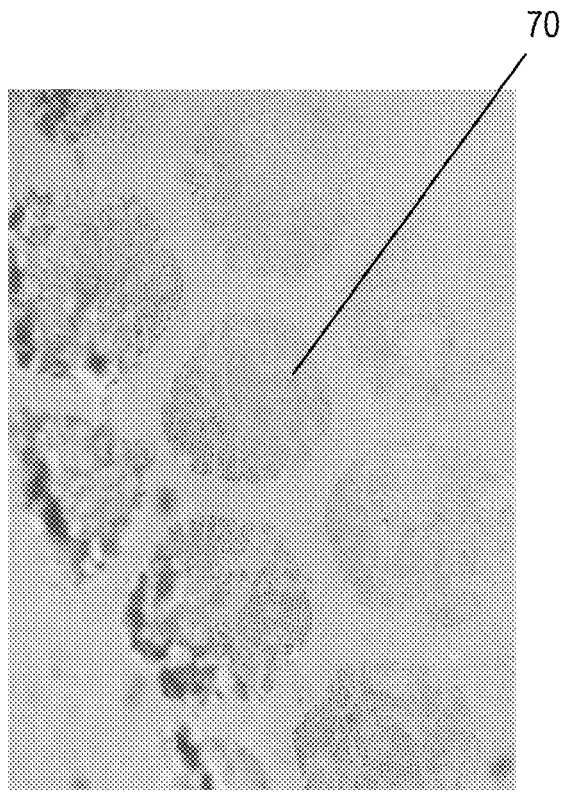
FIGS. 10a and 10b are micrographs depicting punctures in a 10 micron thick cellophane sheet produced by the device of in the present invention.
Figure 10B:
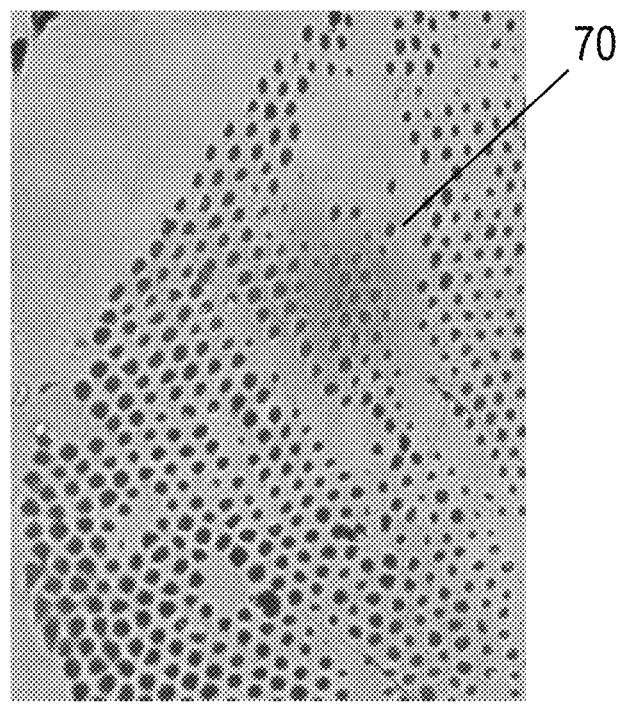

FIGS. 10a and 10b depict an array of punctures 70 formed through a polyethylene sheet having a thickness on the order of 10 microns. FIG. 10a depicts a magnification of approximately 100×. FIG. 10b depicts a magnification of 430×. The array of glass micro-rods included a pitch of approximately 7 microns and each glass micro-rod had a height of approximately 12 microns.

While the present invention has been particularly shown and described with respect to the preferred embodiments thereof, it will be understood by those skilled in the art that the foregoing and other changes in forms of details may be made without departing form the spirit and scope of the present invention. It is therefore intended that the present invention not be limited to the exact forms and details described and illustrated, but fall within the scope of the appended claims.

What is claimed:

1. A medical device for treating recurrent corneal erosions comprising:
    an array of solid glass micro-rods including a sharp feature opposite a solid base of the array of solid glass micro-rods having a penetrating length ranging from 10 microns to 20 microns that punctures a Bowman's layer of an eye, wherein each of the array of solid glass micro-rods have a glass micro-rod diameter that produces punctures in the Bowman's layer with a puncture diameter ranging from 1 micron to 10 microns.

2. The medical device of claim 1, wherein the solid glass micro-rods comprise a silica containing material.

3. The medical device of claim 1, wherein the array of solid glass micro-rods includes a plurality of solid glass micro-rods, wherein adjacent solid glass micro-rods are separated by a distance ranging from about 5 microns to about 40 microns.

4. A medical device for treating recurrent corneal erosions comprising:
    an array of solid glass micro-rods including a sharp feature opposite a solid base of the array of solid glass micro-rods having a length that penetrates a Bowman's layer and epithelial layer of an eye and having a diameter that produces punctures in the Bowman's layer and the epithelial layer with a puncture diameter ranging from 1 micron to 10 microns, wherein adjacent solid glass micro-rods of the array of solid glass micro-rods are separated by a dimension ranging from 10 microns to 20 microns so that substantially each of the solid glass micro-rods of the array of solid glass micro-rods punctures a single basal cell of the epithelial layer.

5. The medical device of claim 4, wherein the solid glass micro-rods comprise a silica containing material.

6. The medical device of claim 4, wherein the length of the sharp feature is less than 50 microns.

7. The medical device of claim 4, wherein the length of the sharp feature ranges from about 10 microns to about 20 microns.

8. The medical device of claim 4, wherein the greatest diameter of the sharp feature that penetrates the Bowman's layer is equal to about 50 microns or less.

* * * * *